United States Patent
Chen et al.

(10) Patent No.: US 8,487,274 B2
(45) Date of Patent: Jul. 16, 2013

(54) STROBOSCOPIC OPTICAL IMAGE MAPPING SYSTEM

(75) Inventors: Liang-Chia Chen, Taipei County (TW); Yu-Jun Lai, Taipei (TW); Wai-Lun Zhang, Taipei (TW); Hung-I Yeh, Taipei (TW)

(73) Assignee: National Taipei University of Technology, Taipei (TW)

( * ) Notice: Subject to any disclaimer, the term of this patent is extended or adjusted under 35 U.S.C. 154(b) by 0 days.

(21) Appl. No.: 13/473,820

(22) Filed: May 17, 2012

(65) Prior Publication Data
US 2012/0292529 A1    Nov. 22, 2012

(30) Foreign Application Priority Data
May 17, 2011    (TW) .............................. 100117254 A

(51) Int. Cl.
*G01J 1/58* (2006.01)
*G01N 21/64* (2006.01)

(52) U.S. Cl.
USPC ..................................................... 250/458.1

(58) Field of Classification Search
USPC .......................................... 250/458.1, 459.1
See application file for complete search history.

(56) References Cited

U.S. PATENT DOCUMENTS
6,680,780 B1    1/2004    Fee
2008/0188727 A1    8/2008    Benaron et al.

OTHER PUBLICATIONS

Svrcek et, al., "Characteristics of motion artifacts in cardiac optical mapping studies", Sep. 2-6, 2009, pp. 3240-3243, 31st Annual International Conference of the IEEE EMBS, Minneapolis, Minnesota, USA.
Inagaki et, al, "High resolution optical mapping of cardiac action potentials in freely beating rabbit hearts", Sep. 1-5, 2004, pp. 3578-3580,Proceedings of the 26th Annual International Conference of the IEEE EMBS, San Francisco, CA, USA.

*Primary Examiner* — Mark R Gaworecki
(74) *Attorney, Agent, or Firm* — WPAT, PC; Justin King

(57) ABSTRACT

The present invention provides a stroboscopic optical image mapping system comprising a control module, an optical module, and an image acquiring unit. The control unit forms a delayed pulse signal by modulating a first pulse signal having a plurality of pulses with a pulse period, wherein a time interval between two adjacent pulses of the delayed pulse signal has a time difference with respect to the pulse period. The optical module provides an incident light to be projected on an organic object, which has a dye therein and is stimulated by a second pulse signal for generating a sequential action potential. The fluorescence generates from the dye inside the organic object, which corresponds to the intensity of the sequential action potential. The image acquiring unit is actuated to acquire the fluorescent light according to the delayed pulse signal, thereby forming a plurality of fluorescent images.

23 Claims, 15 Drawing Sheets

STROBOSCOPIC OPTICAL IMAGE MAPPING SYSTEM

FIELD OF THE INVENTION

The present invention relates an optical system, and more particularly, to a stroboscopic optical image mapping system.

BACKGROUND OF THE INVENTION

The organic object which includes excitable cells such as neurons or cardiomyocytes can generate action potentials. Under physiologic condition, cellular membrane potential is induced through ion permeability between the inner and the outer sides of the membrane in excitable cells. The excitable cells are responsible for cell-cell communication and triggering action potential.

Electrophysiology is a study that investigates the electrical properties in living cells and tissues while cardioelectrophysiology is the study focusing on cardiomyocytes or cardiac tissues.

Cardioelectrophysiology is a major index for studying the cardiac function and cardiac pathology. Optical image mapping system is one of powerful tools for analyzing cardioelectrophysiology; however, conventional optical image mapping systems still have remaining drawbacks and need to be solved.

Conventional optical image mapping system 1 illustrated in FIG. 1 mainly comprises an optical instrument 11 for inspecting cardiac tissues or organic objects 10 disposed on a platform 13, and an image acquiring unit 12. The optical instrument 11 further comprises a light source 110, a collimating lens 111, a beam splitter 112, a filter 113, and lens 114. In the optical image mapping system 1, the cellular membrane potential can be altered during variation period of action potential, so the chemical resonant structures of the voltage-sensitive dye is changed accordingly. The excition fluorescence generated by the voltage-sensitive dye will be transformed to the image acquiring unit.

The fluorescent light signals are amplified by the optical instrument 11 and recorded by the image acquiring unit 12 such as charge-coupled device (CCD). The optical image mapping system 1 for assisting the research of cardioelectrophysiology is irreplaceable due to merits of (1) collecting variation of cellular membrane potential signals by an optical scanning without contacting the tissue; (2) providing superior spatial and temporal resolution of action potential signals than obtained by the array electrodes inspection; (3) preventing the electrical noise interference in the recorded electrical signals. Despite of the merits described above, however, the conventional optical image mapping system requires image acquiring unit having high speed camera and massive image files storage media, so the cost of the system is going expensive. Meanwhile, the limits of required inspection time and image resolution are also the causes that the optical image mapping system can't be commonly applied in the field of electrophysiology.

In addition, conventional arts like US. Pub. No. 2008/0188727 disclosed an improved spectroscopy illuminator for generating broadband light and for delivering the light to a sample with an improved delivery efficiency, for higher optical density and/or reduced thermal transfer uses a solid-state broadband white LED to produce broadband light, which is then transmitted to a sample region, such as a living tissue or blood in vivo or a biological sample in a spectrophotometer target region. The solid-state source keeps both the illuminator and sample cool during operation, allowing the illuminator to be integrated into the tip of a medical probe, a medical system such as an oximeter, or other monitoring systems or devices making measurements based on light scattering, absorbance, fluorescence, phosphorescence, Raman effects, use of a contrast agent, or other known spectroscopy techniques.

Besides, U.S. Pat. No. 6,680,780 also discloses a method and system to actively stabilize a probe mounted on a manipulator such that the probe moveable in response to a control voltage. A laser interferometer is utilized to transmit a first light beam to the subject and to receive a reflected light beam, to modulate a second light beam with a radio frequency signal to form a reference light beam, and to combine the reflected light beam and the reference beam to form an interference pattern. A demodulator is utilized to demodulate a phase shift of a radio frequency component of the interference pattern to determine a displacement signal representative of an amount and direction of subject movement, and to convert the displacement signal to the control voltage. The probe is then moved in response to the control voltage, providing stabilization relative to subject movement, and the probe may then be utilized for desired measurements within the subject.

SUMMARY OF THE INVENTION

The present invention provides an optical image mapping system using stroboscopic and delay control for acquiring a plurality of fluorescent images with respect to an organic object in a stimulated status, wherein each fluorescent image corresponding to a specific delayed time point. The plurality of fluorescent images are converted and recombined into a plurality of processed signal sequences by means of image processing and filter processing, and the processed signal sequences can be utilized to be a basis for determining electrophysiology of the organic object.

The present invention provides an optical image mapping system using stroboscopic and delay control for observing bio-transformation of an organic object in high spatial and temporal resolution, nondestructive, and contactless way without using an expansive image acquiring unit. In addition, the stroboscopic optical image mapping system has superior sensitivity for obtaining high-resolution fluorescent images, which improve the follow-up image process and calculation of the electrophysiologic analysis.

In one embodiment, the present invention provides a stroboscopic optical image mapping system, comprising a control module, an optical module, and an image acquiring unit. The control module performs a delay control on a first pulse signal which has a plurality of pulses formed by a pulse period, thereby generating a delayed pulse signal wherein a time interval between two adjacent pulses of the delayed pulse signal has a time difference with respect to the pulse period. The light source module provides an incident light projected on an organic object with a dye contained therein, wherein the organic object is stimulated by a second pulse signal thereby generating a sequential action potential, and the incident light excites the dye inside the organic object such that the organic object generates a fluorescent light corresponding to the intensity of the sequential action potential. The image acquiring unit, coupled to the control module, acquires the fluorescent light according to the delayed pulse signal, thereby forming a plurality of fluorescent images.

In another embodiment, the present invention provides a stroboscopic optical image mapping system, comprising a control module, a light source module, and an image acquiring unit. The control module performs a delay control on a first pulse signal which has a plurality of pulses formed by a pulse period, thereby generating a delayed pulse signal wherein a time interval between two adjacent pulses of the delayed pulse signal has a time difference with respect to the pulse period. The light source module, coupled to the control module, provides an incident light to be projected on an organic object with a dye contained therein, wherein the organic object is stimulated by a second pulse signal, thereby generating a sequential action potential, and the incident light excites the dye inside the organic object such that the organic object generates a fluorescent light corresponding to the intensity of the sequential action potential. The image acquiring unit acquires the fluorescent light so as to form a plurality of fluorescent images.

BRIEF DESCRIPTION OF THE DRAWINGS

The present invention will become more fully understood from the detailed description given herein below and the accompanying drawings which are given by way of illustration only, and thus are not limited in the present invention and wherein.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as the follows.

Figure 1:
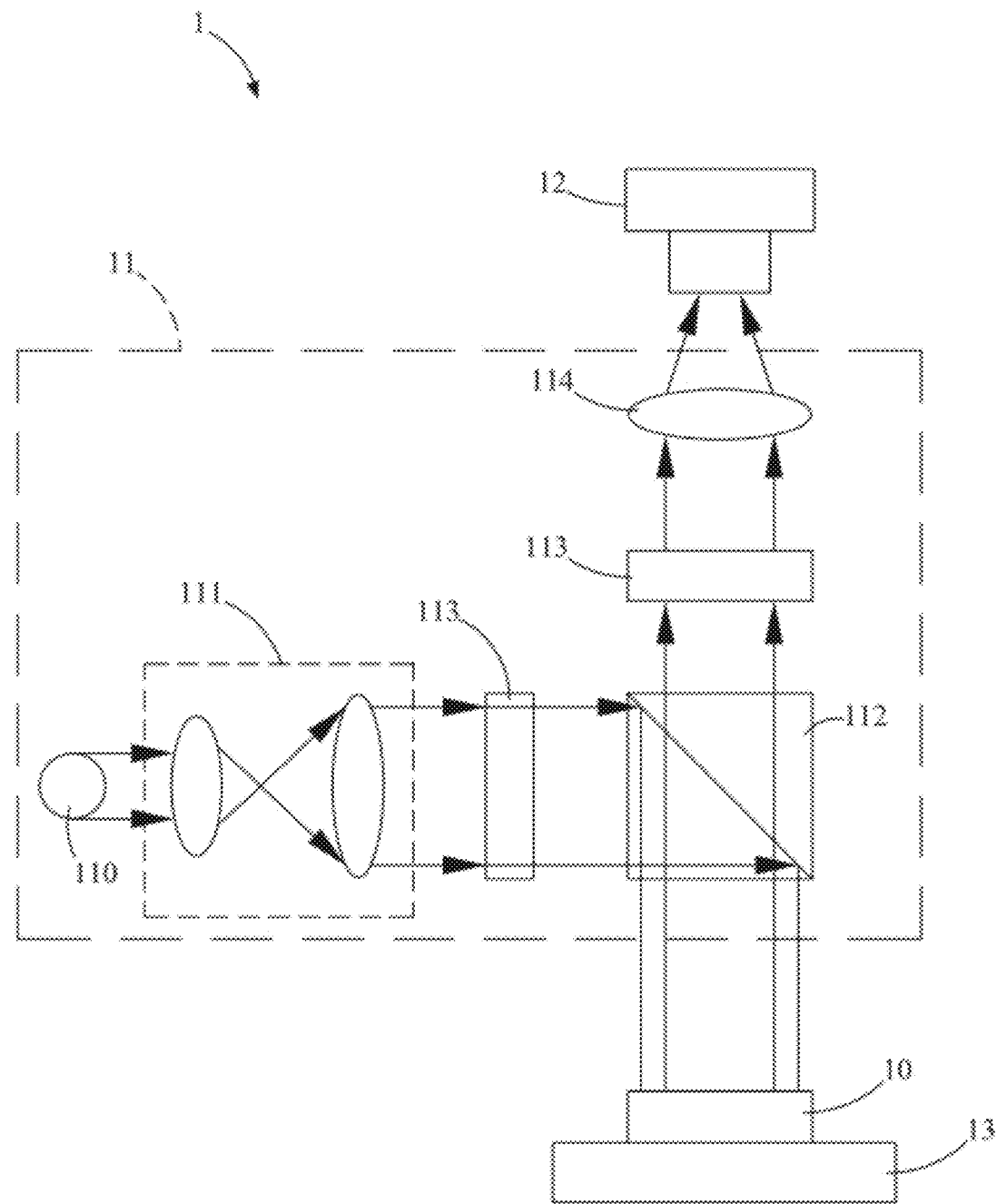
FIG. 1 illustrates a conventional optical image mapping system.
Figure 2A:
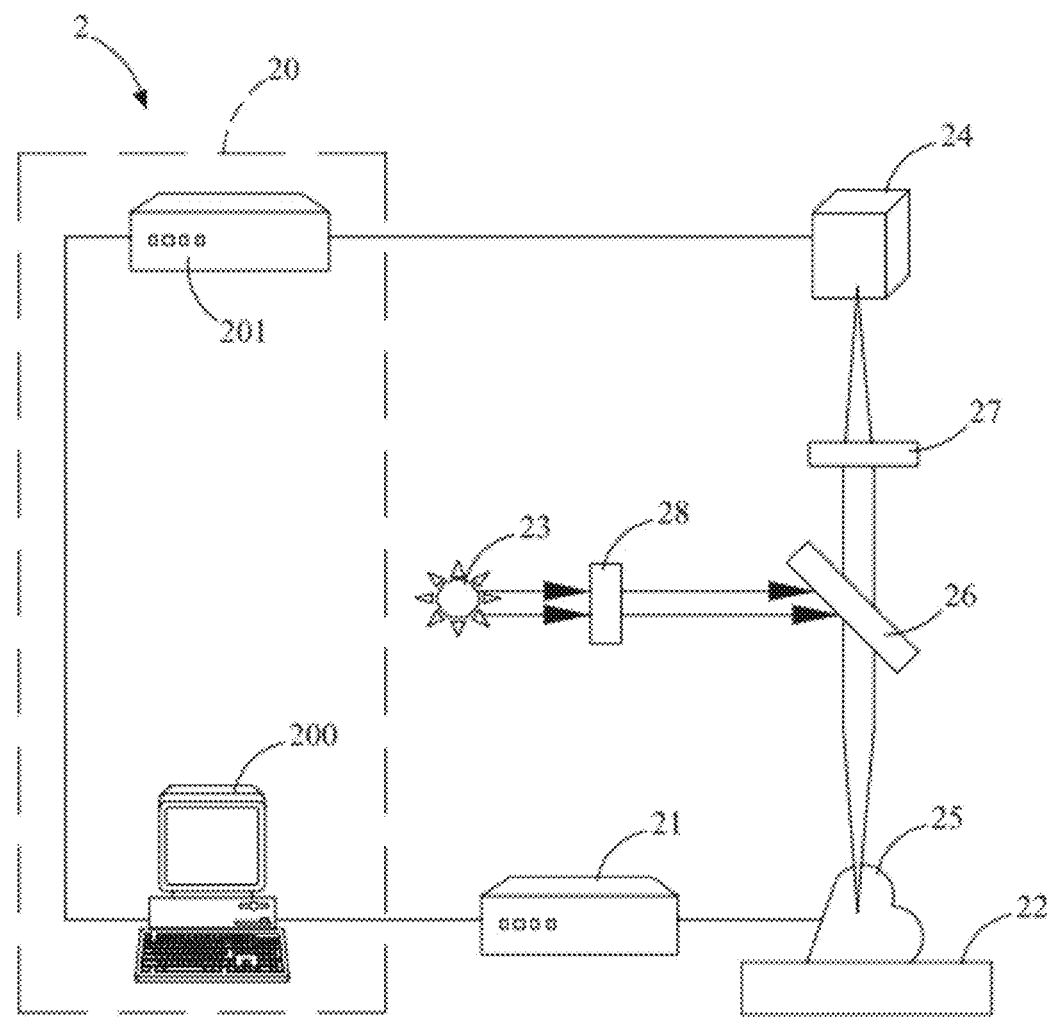
FIG. 2A illustrates a first embodiment of the stroboscopic optical image mapping system according to the present invention.
Figure 3A:
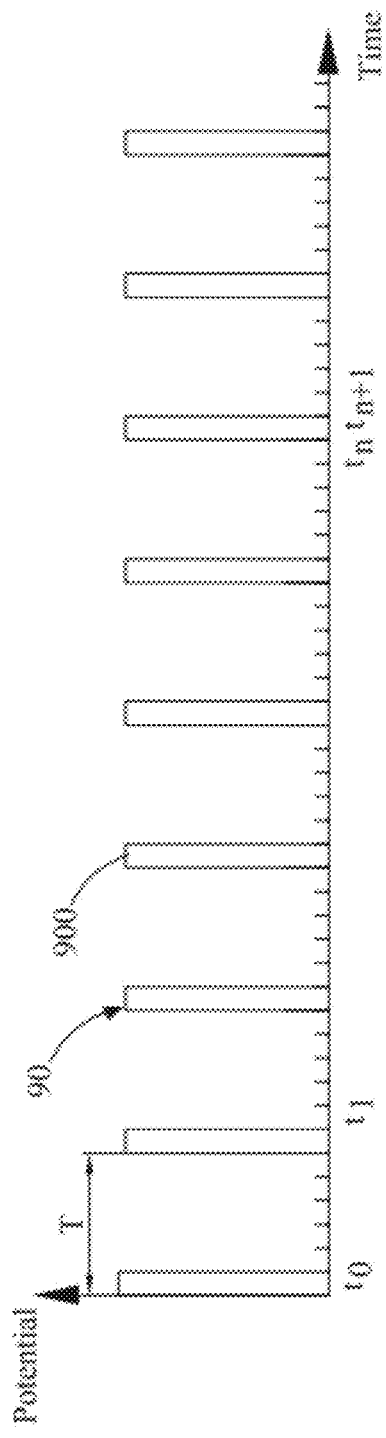
FIG. 3A illustrates a first pulse signal according to the present invention.

Please refer to FIG. 2A, which illustrates a first embodiment of the stroboscopic optical image mapping system according to the present invention. In the present embodiment, the stroboscopic optical image mapping system 2 comprises a control module 20, an electrical stimulator 21, a platform 22, a light source module 23, and an image acquiring unit 24. The control module 20 performs a delay control on a first pulse signal so as to form a delayed pulse signal. Please refer to FIG. 3A, which illustrates a first pulse signal according to the present invention. The first pulse signal 90 is composed of a plurality of pulses 900 formed by a pulse period T. Please refer to FIG. 3B, which illustrates a delayed pulse signal according to the present invention. To achieve the objective of stroboscopic image acquisition, the control module 20 adjusts a trigger timing of each pulse 900 through the delay control such that a time interval $\Delta T$ between two adjacent pulses 910 of the delayed pulse signal 91 has a time difference $\Delta t$ with respect to the pulse period T of the first pulse signal 90.

Figure 3B:
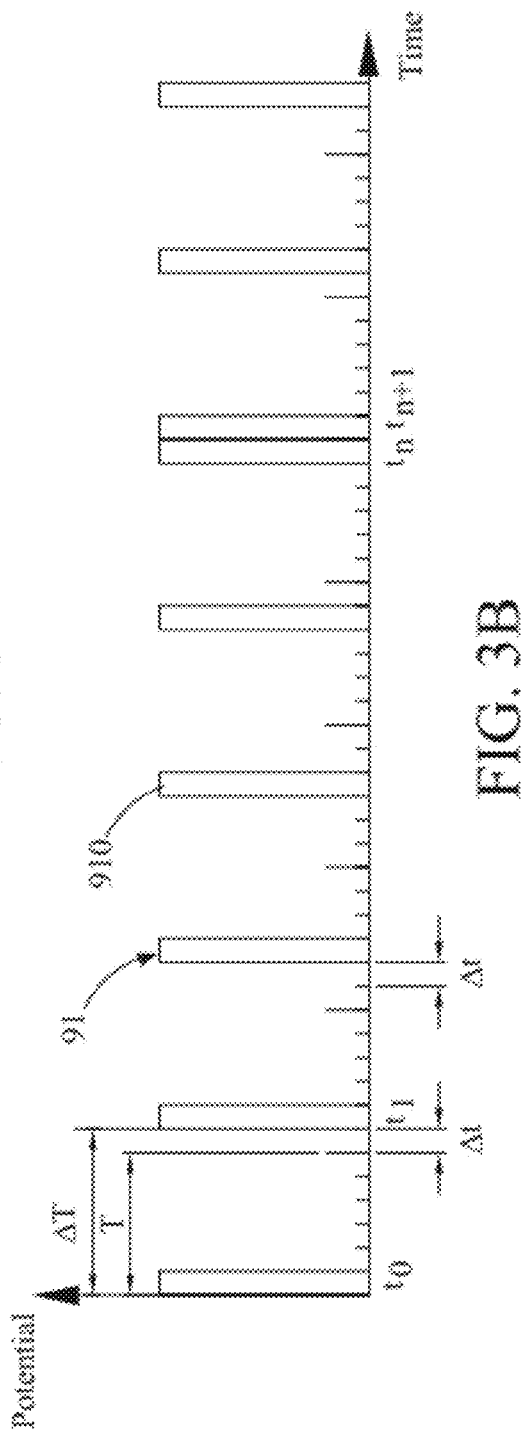
FIG. 3B illustrates a delayed pulse signal according to the present invention.

In FIG. 3B, it is shown that the time interval $\Delta T$ between the initial triggered pulse at an initial time point $t_0$ and the first triggered pulse at the first time point $t_1$ has the time difference $\Delta t$ with respect to the pulse period T. When the accumulated time difference from the first time point to the $n^{th}$ time point is equal to the pulse period T, at the $n+1^{th}$ time point, the triggered state will be returned to the state like the initial time point $t_0$, and the following triggered states will be repeated periodically like the state from the initial time point to the $n^{th}$ time point.

Please refer back to FIG. 2A, in the present embodiment; the control module 20 further comprises a controller 200 and a first delay unit 201. The controller 200 is utilized to provide the first pulse signal shown in FIG. 3A. It is known that the controller 200 can be, but should not be limited to a computer, workstation or a server, which is able to generate the first pulse signal. Alternatively, the controller 200 can also be a separated pulse generator to be combined with a computer, workstation or a server.

The first delay unit 201 is coupled to the controller 200 and the image acquiring unit 24. The first delay unit 201 is utilized to perform the delay control on the first pulse signal generated by the controller 200 such that the time interval between the two adjacent pulses triggered at a different time point has the time difference with respect to the pulse period, which is respectively shown in FIG. 3A and FIG. 3B. It is noted that although the first delay unit 201 shown in FIG. 2A is separated from the controller 200, alternatively, in another embodiment, the delay unit 201 is capable of being combined with the controller 200, thereby forming an integrated control module. The one skilled in the art would recognize that a variety of control module may be used according to the basis and scope of the foregoing disclosure.

The electrical stimulator 21 can generate a second pulse signal. The platform 22 carries an organic object 25, which can be a biological tissue such as nervous, mussel, or cardiac tissues. In the present embodiment, the organic object 25 is a cardiac tissue. The cardiac tissue carried by the platform 22 contains a depressant and a dye, and is coupled to the electrical stimulator 21 for receiving the second pulse signal. When the organic object 25 receives the second pulse signal, it is capable of generating a sequential action potential. Generally speaking, the organic object 25 will be actuated to vibrate due to receiving the second pulse signal. It is noted that the second pulse signal is not limited to the external pulse signal but can also be a physiological signal generated by the organic object 25 instead. Since the depressant is contained inside the organic object 25, the motion actuated by the second pulse signal will be depressed. In the present embodiment, the depressant can be, but should not be limited to, a Cytochalasin D (Cyto D). It is noted that, in addition to utilizing the depressant as a depressing means, a depressing element 29 shown in FIG. 2D, such as a cover slide, covering on the organic object 25 carried by the platform 22 can also be an alternative to depress the motion generated by the organic object 25. Besides, the dye inside the organic object 25 is a voltage-sensitive dye which is sensitive to the membrane potential of the organic object 25. The dye can be, but should not be limited to, di-4-ANEPPs.

The optical module 23 projects an incident light matching with the dye in the organic object 25. Since the incident light matches with the dye, the incident light excites the dye inside the organic object 25 such that the organic object 25 generates a fluorescent light corresponding to the intensity of the sequential action potential. In the present embodiment, the optical module 23 can be, but should not be limited to, a light emitting diode (LED). In the present embodiment, the wavelength of the excitation is 475 nm and emission is 617 nm. It is noted that the wavelength of fluorescence having the maximum efficiency of the incident fluorescence is determined according to the type of the dye, so it will not be limited to the present embodiment.

The image acquiring unit 24 is coupled to the control module 20, and acquires the fluorescent light according to the delayed pulse signal so as to form a plurality of fluorescent images with respect to the organic object 25. Please refer to FIG. 3B, when each pulse of the delayed pulse signal is generated, the image acquiring unit 24 is triggered by each pulse so as to acquire one fluorescent image. The image acquiring unit 24 can be selected to be a charge-coupled device (CCD), or a complementary metal-oxide-semiconductor (CMOS). In addition, a dichroic beam splitter 26 and wavelength filter 27 and 28 are disposed between the image acquiring unit 24 and organic object 25, whereby the wavelength efficiency can be kept in optimum status, and the CCD can be prevented from being effected by the stray light.

Figure 2B:
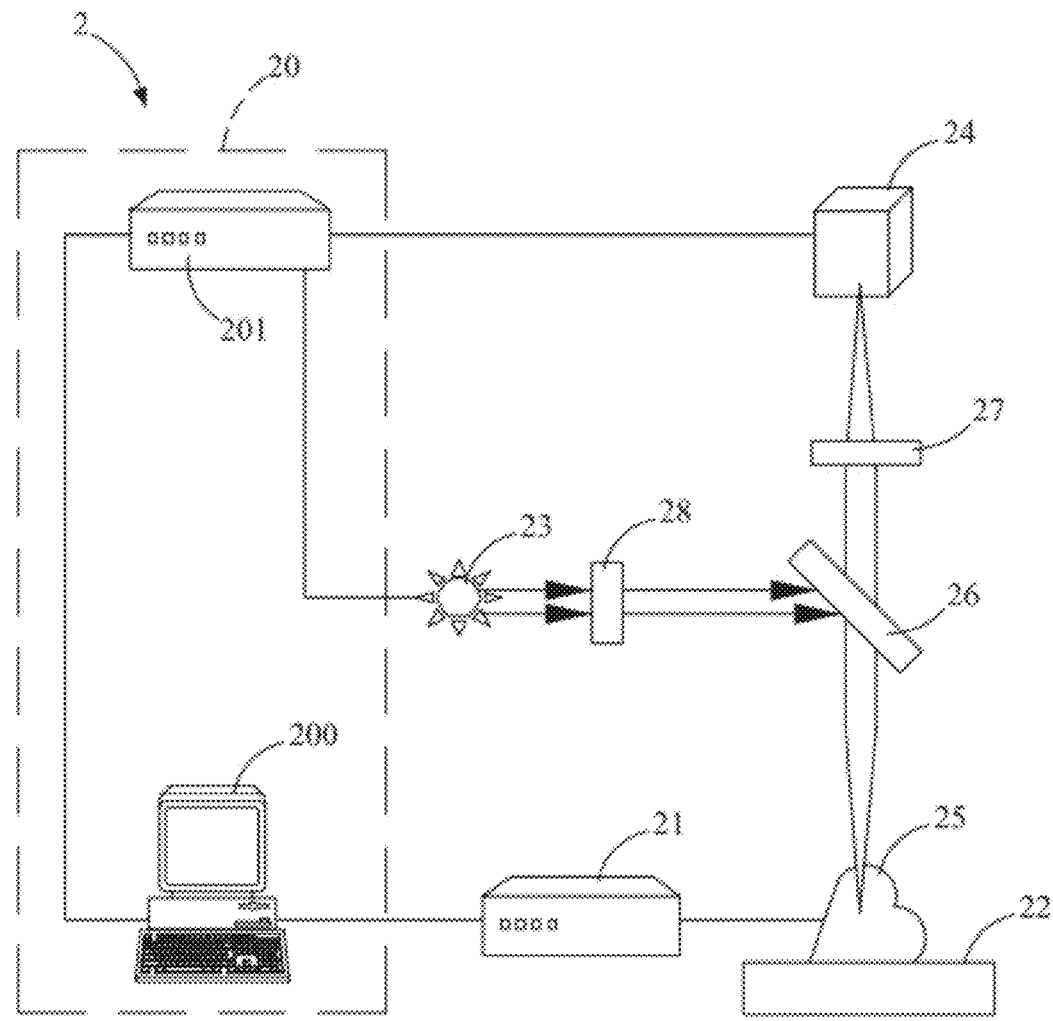
FIG. 2B illustrates a second embodiment of the stroboscopic optical image mapping system according to the present invention.
Figure 2C:
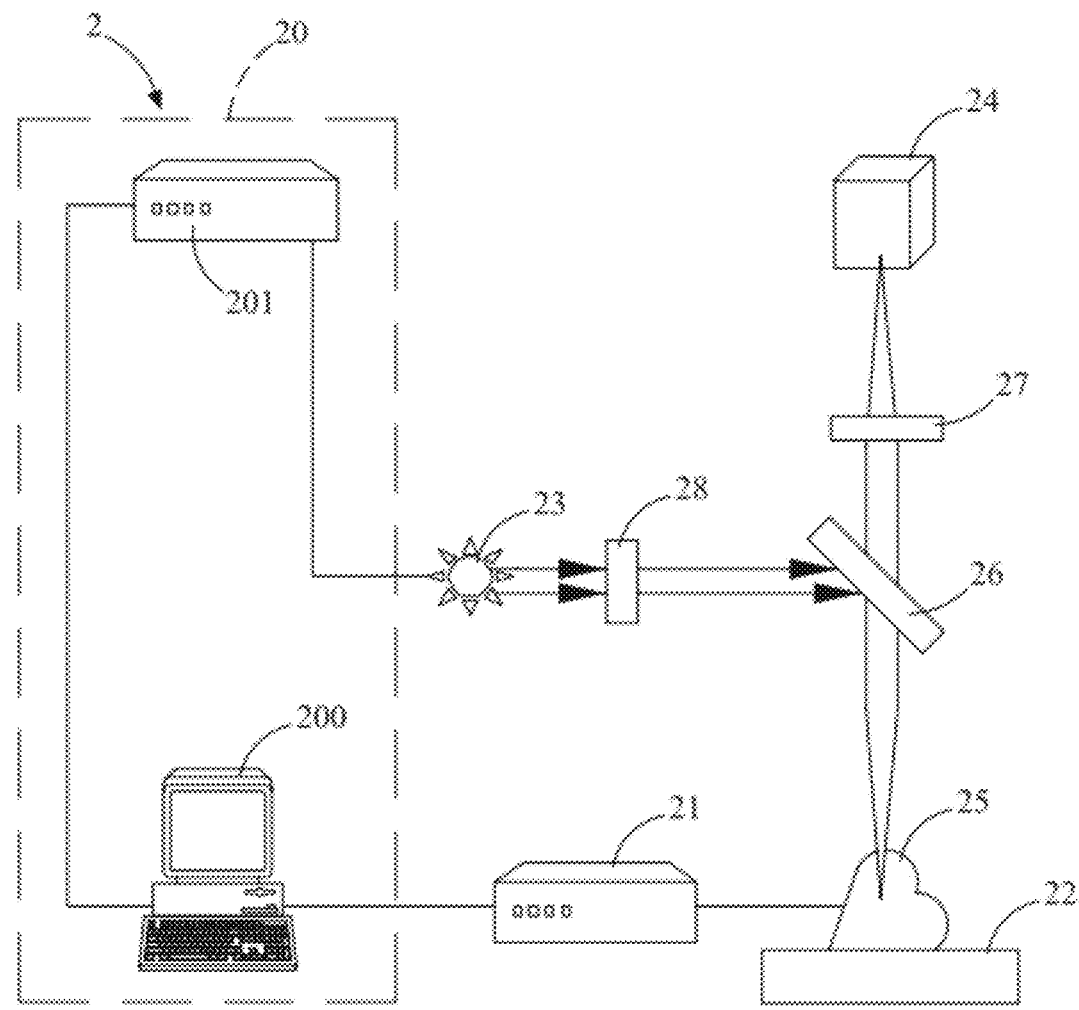
FIG. 2C illustrates a third embodiment of the stroboscopic optical image mapping system according to the present invention.
Figure 2D:
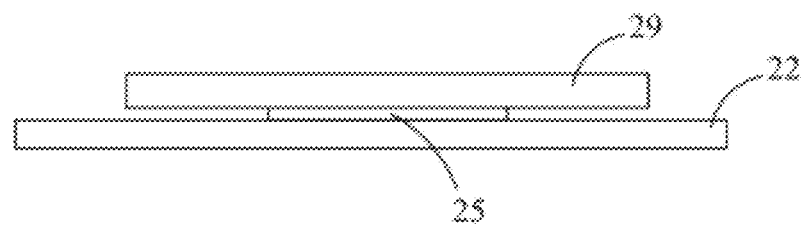
FIG. 2D illustrates a cover slide pressing on an organic object.

In addition to the architecture shown in FIG. 2A, the FIG. 2B also illustrates a second embodiment of the stroboscopic optical image mapping system according to the present invention. In the embodiment shown in FIG. 2B, a main difference from the embodiment shown in FIG. 2A is that the control module 20 provides the delayed pulse signal to the optical module 23 and the image acquiring unit 24 in the mean time such that the frequency for generating the incident light by the optical module 23 is synchronized to the image acquiring frequency of the image acquiring unit 24. Please refer to FIG. 2C, which illustrates a third embodiment of the stroboscopic optical image mapping system according to the present invention. The embodiment shown in FIG. 2C is similar to the embodiment shown in FIG. 2A basically, and the difference is the control module 20 only provides the delayed signal to the optical module 23 so as to control the frequency for generating the incident light.

After acquiring the plurality of fluorescent images by the image acquiring unit 24 of the stroboscopic optical image mapping system shown in FIG. 2A, 2B or 2C, the control module 20 performs an image and signal process on those acquired fluorescent images, which will be described further in detail below. Please refer to FIG. 4A, which illustrates a relationship between the delayed pulse signal and the sequential action potential generated by the excited organic object. For saving the cost of the system, the image acquiring unit in the present invention may be a low speed image acquiring unit. To obtain the potential variation transformed from the fluorescent light emitted by the organic object through the low speed image acquiring unit, each pulse corresponding to a specific time point in the delayed pulse signal is utilized to trigger the image acquiring unit to acquire the fluorescent light with respect to a specific segment of one action potential wavelet composing the sequential action potential. Thereafter, the acquired image corresponding to the specific time segment is processed and recombined to form a recombined potential signal, which can be utilized to be a basis for determining the electrophysiologic condition of organic object.

Figure 4A:
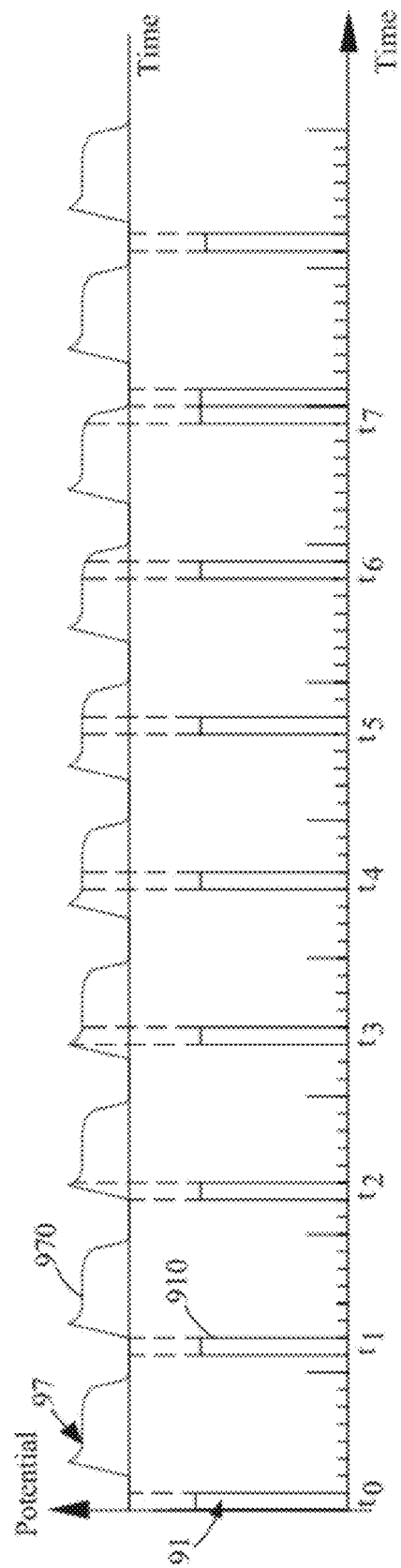
FIG. 4A illustrates a relationship between the delayed pulse signal and the sequential action potential generated by the organic object.
Figure 4B:
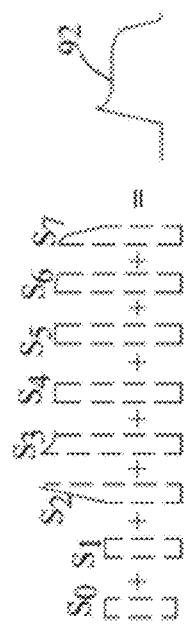
FIG. 4B illustrates a recombination process for forming a recombined action potential.
Figure 4C:
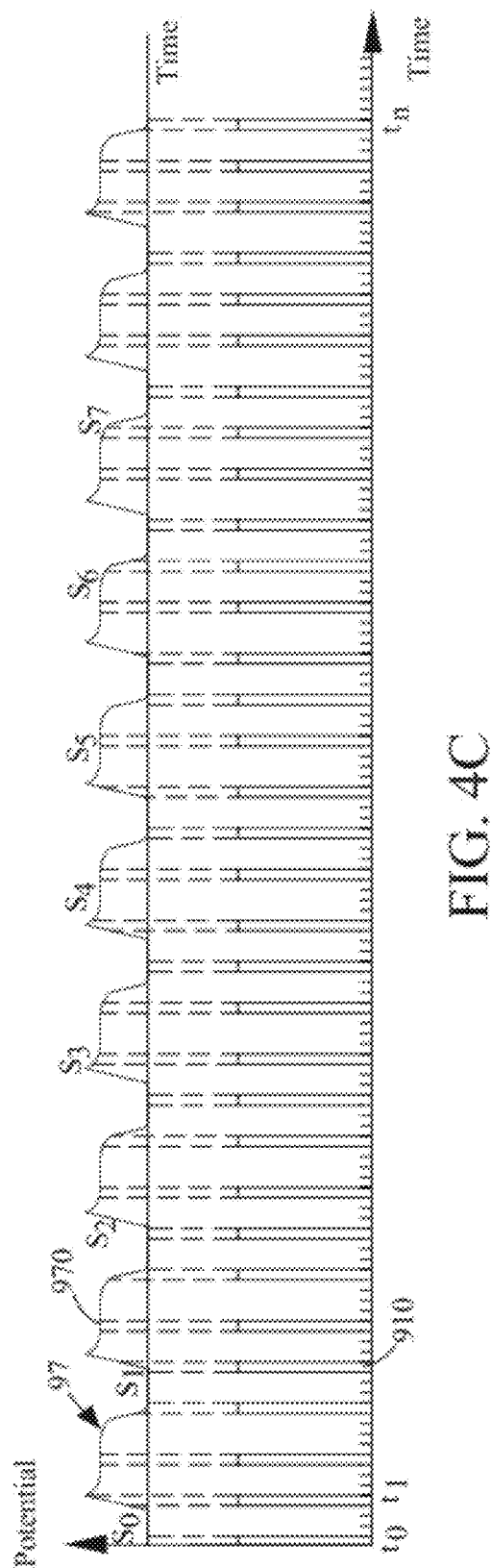
FIG. 4C illustrates another recombination process for forming a recombined action potential.

In FIG. 4A, numeral 97 represents the sequential action potential generated from the organic object actuated by the second pulse signal, wherein the sequential action potential is composed of a plurality of action potential wavelets 970. Meanwhile, the numeral 91 represents a delayed pulse signal composed of a plurality of pulses 910. In the present embodiment, each action potential wavelet 970 corresponds to one pulse 910 having a phase shift with the pulse in the previous time point. When each pulse 910 is generated, the image acquiring unit 24 is capable of generating one corresponding fluorescent image associated with the specific segment of one action potential wavelet 970. Please refer to FIG. 4B, which illustrates a recombination process for forming a recombined action potential. The notation $s_0$~$s_7$, respectively, refer to the potential signals converted from the fluorescent images, respectively, corresponding to the specific segment of each action potential wavelet 970. Although the fluorescent image generated by the image acquiring unit triggered by each pulse signal corresponds to a different segment of the sequential action potential, it is capable of recombining potential signals $s_0$~$s_7$, respectively, corresponding to each fluorescent image at different time segment by the signal process so as to form the recombined potential signal 92. In the embodiment shown in FIG. 4B, the recombined potential signal 92 is formed by combining eight different segments, respectively, obtained from eight fluorescent images respectively corresponding to eight action potential wavelets in sequence. After repeating a plurality of times, a plurality of recombined potential signals can be formed. It is noted that, in embodiment shown in FIGS. 4A and 4B, each action potential wavelet 970 is corresponding to only one pulse 910 of the delayed pulse signal 91. Alternatively, in another embodiment shown in FIG. 4C, each action potential wavelet 970 is corresponding to a plurality of pulses 910 generated by a faster pulse signal such that the quantities of action potential wavelets 970 for forming one recombined potential signal can be reduced, thereby increasing the efficiency of recombination.

Figure 5A:
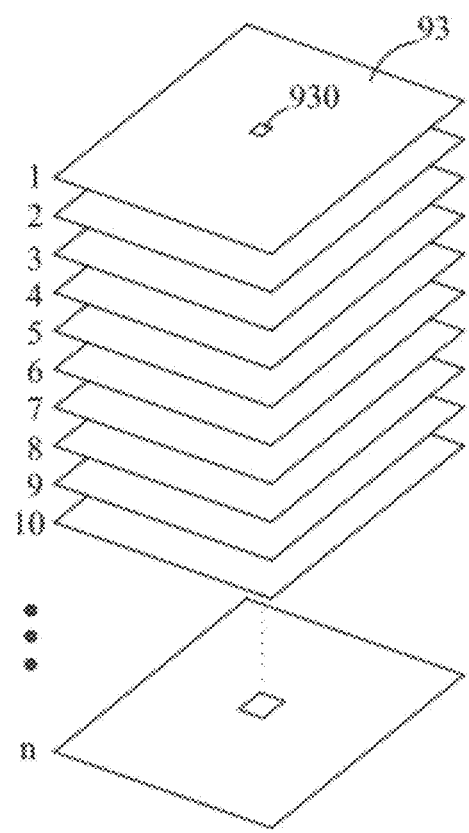
FIGS. 5A and 5B illustrate a relationship between the plurality of fluorescent images and the recombined potential signal of a related area of the organic object according to the present invention.
Figure 5B:
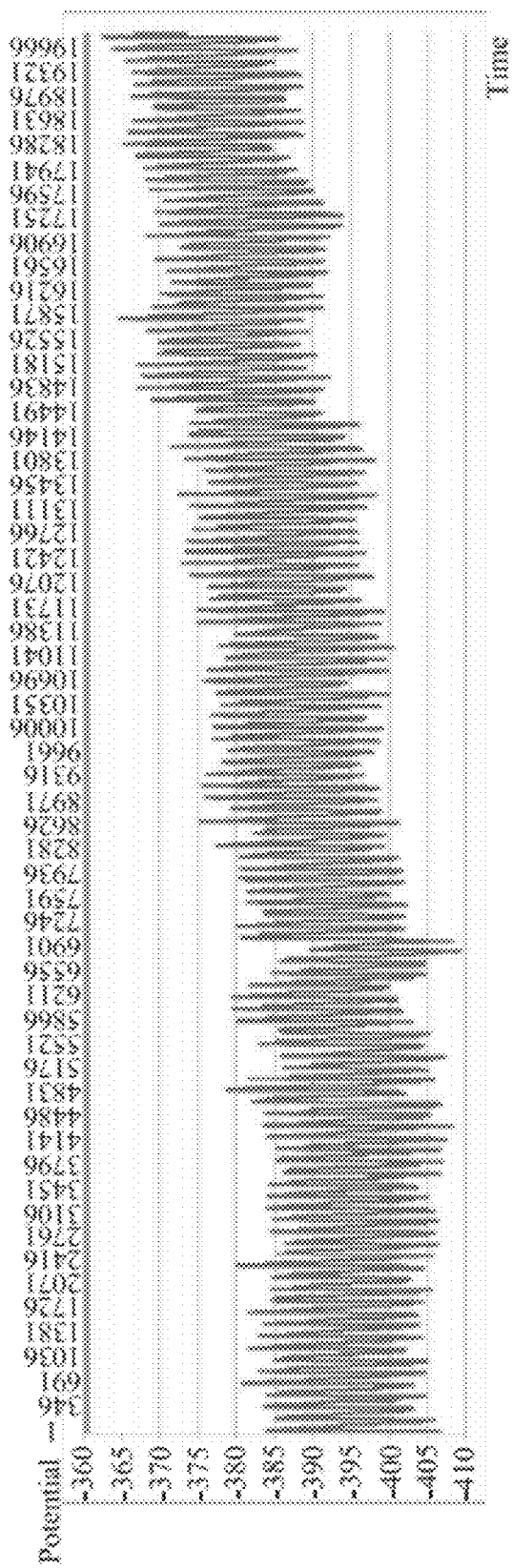
Figure 5C:
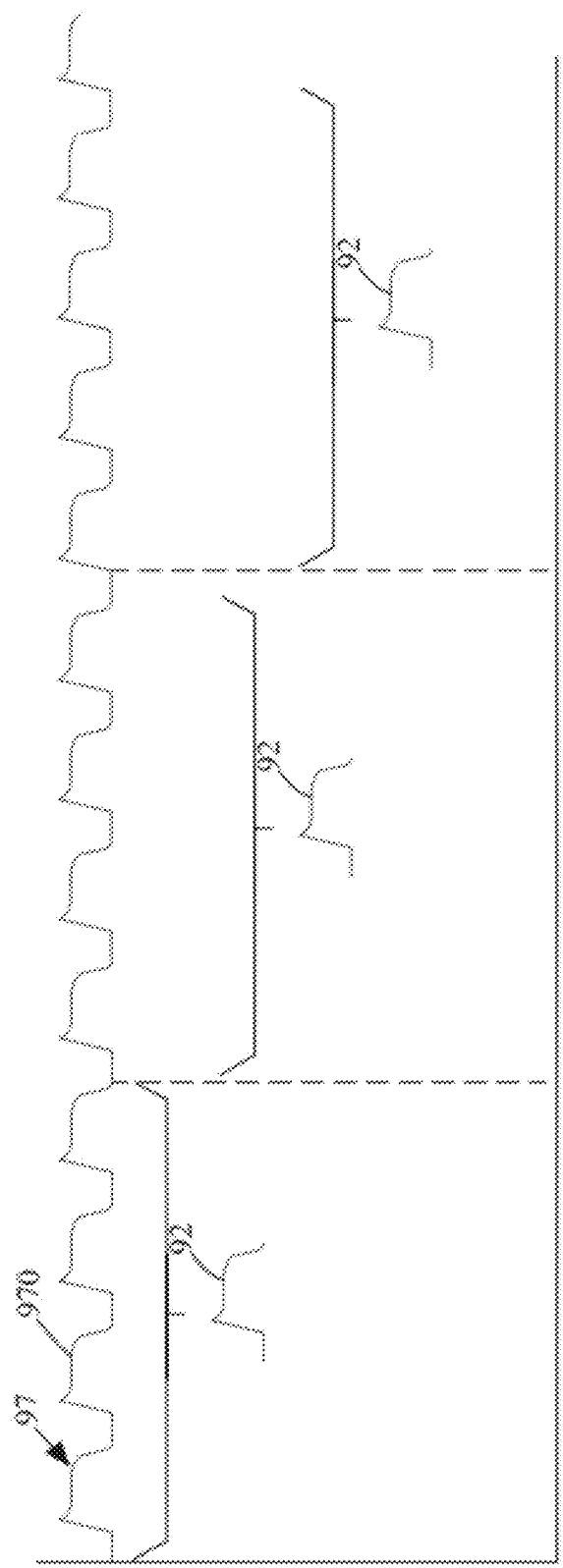
FIGS. 5C and 5D respectively illustrate process for recombining potential signals.
Figure 5D:
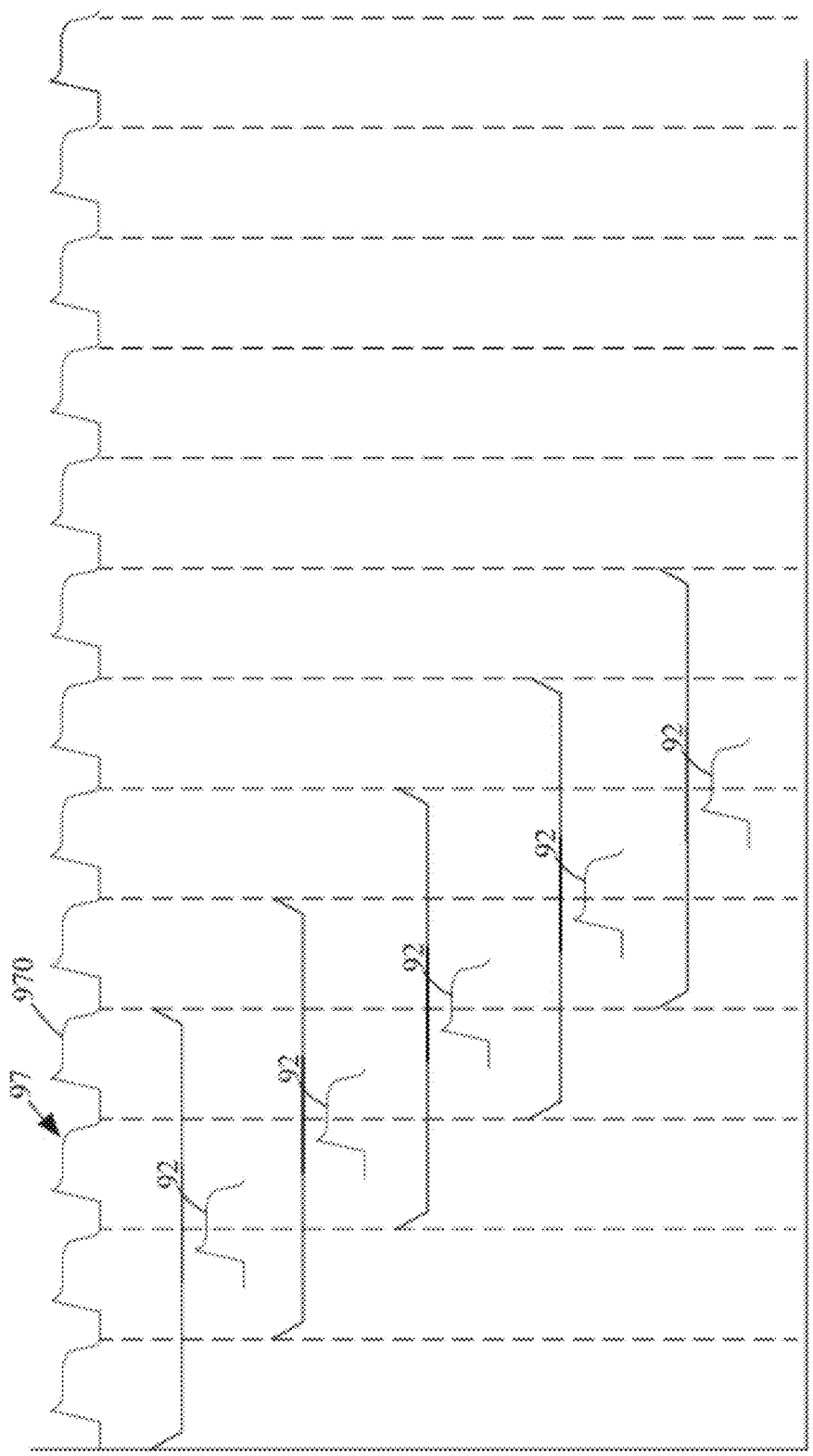

Next, please refer to FIGS. 5A and 5B, which illustrate a relationship between the plurality of fluorescent images and the recombined potential signal of a related position of the organic object according to the present invention. In FIG. 5A, a plurality of fluorescent images 93 are captured by the image acquiring unit. Each pixel in each fluorescent image represents a related position of the organic object. In FIG. 5B, it illustrates a signal sequence converted from the fluorescent images with respect to the related position 930 of the organic object shown in FIG. 5A, accordingly, FIGS. 5C and 5D illustrate the process for recombining signals. In FIG. 5C, the recombined potential signal 92 is composed of a plurality of segments, respectively, acquired from a plurality of action potential wavelets 970 according to the principle shown in FIGS. 4A-4C, wherein each recombined potential signal 92 is composed of four action potential wavelets 970 in this embodiment. Meanwhile, the time interval between the two adjacent recombined potential signals 92 is equal the time interval for forming four action potential wavelets 970. It is noted that the quantities of the action potential wavelets for recombining the recombined potential signal is determined according to the need of the user, it should not be limited to four action potential wavelets in this embodiment. Alternatively, FIG. 5D illustrates another embodiment for recombining the recombined potential signal. In the embodiment shown in FIG. 5D, when the first recombined potential signal 92 is recombined by using the first to fourth action potential wavelets 970, it is not necessary to use another four action potential wavelets to form the second recombined potential signal like the result shown in FIG. 5C but only to recombine the fifth action potential wavelet and the last three (the second, the third, and the fourth) action potential wavelets corresponding to the first recombined signal, thereby forming the second recombined potential signal, whereby the time efficiency for forming the recombined potential signal can be enhanced.

After the recombination process, if the filtering process is not properly preceded, the recombined potential signals shown in FIG. 5B usually have a lot of noise interferences, thereon such that the recombined potential signals is difficult to be distinguished. Accordingly, before the recombination process, it can further perform a spatial filtering process on the fluorescent images. In the present embodiment, the spatial filtering process on the plurality of fluorescent images is performed by the control module, thereby forming a plurality of processed images. It is noted that the spatial filtering process can be, but should not be limited to, a pixel average process, a Gaussian process, and a combination of Gaussian smooth process and pixel average process. In the present invention, the Gaussian smooth process and pixel average process are utilized by the control module to filter out the noise within the fluorescent images.

Figure 6A:
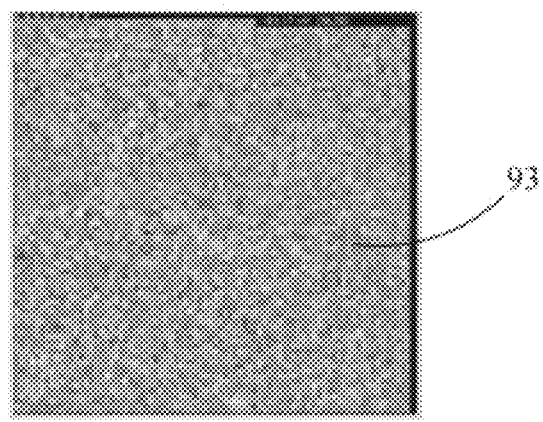
FIGS. 6A to 6C illustrate the images processed by the spatial filtering process.
Figure 6B:
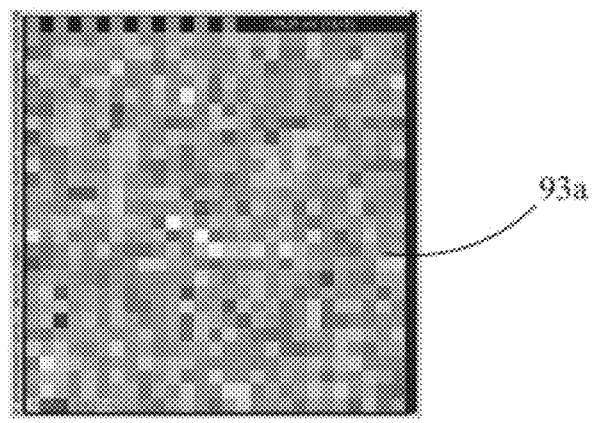
Figure 6C:
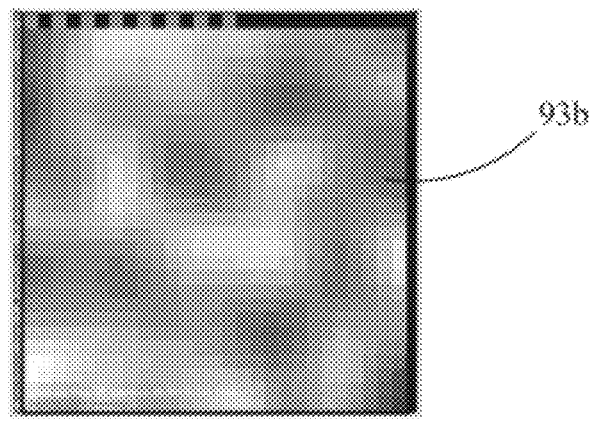

Please refer to FIGS. 6A to 6C, which illustrate a sequential variation during the spatial filtering process on the fluorescent images. Taking a single fluorescent image as an example, FIG. 6A represents a fluorescent image 93 and FIG. 6B represents a processed image 93a after the pixel average process, wherein the pixel average process is performed by averaging the brightness value of pixels within a three-by-three pixel square. FIG. 6C represents another processed image 93b, which is a result after processing the image 93a through the Gaussian smooth process. It is noted that the detail for performing the pixel average process and the Gaussian smooth process is a well-known art, and the spatial filtering process should not be limited to the foregoing pixel average process and Gaussian smooth process, and the one skilled in the art would recognize that a variety of spatial filtering process may be used according to the need.

Figure 7A:
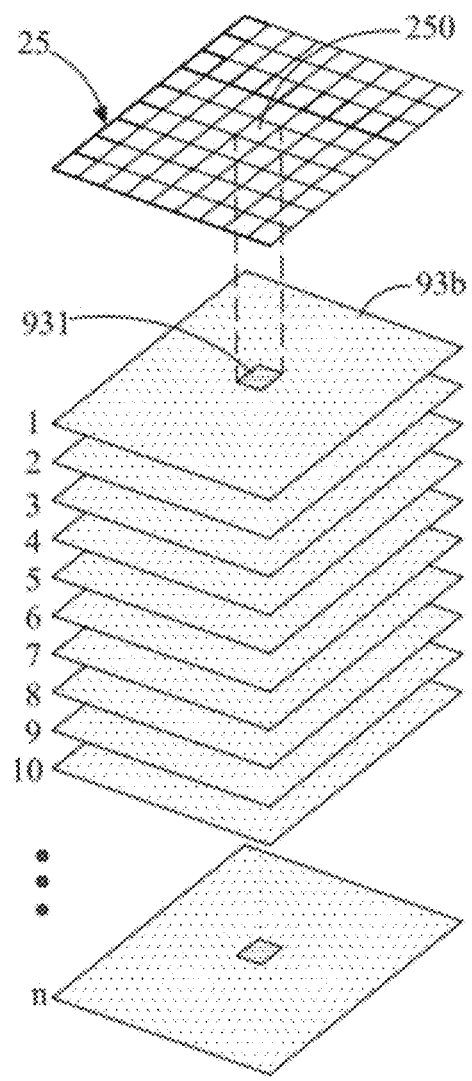
FIGS. 7A and 7B, which illustrates a processed signal sequence with respect to a related area within the plurality of fluorescent images.
Figure 7B:
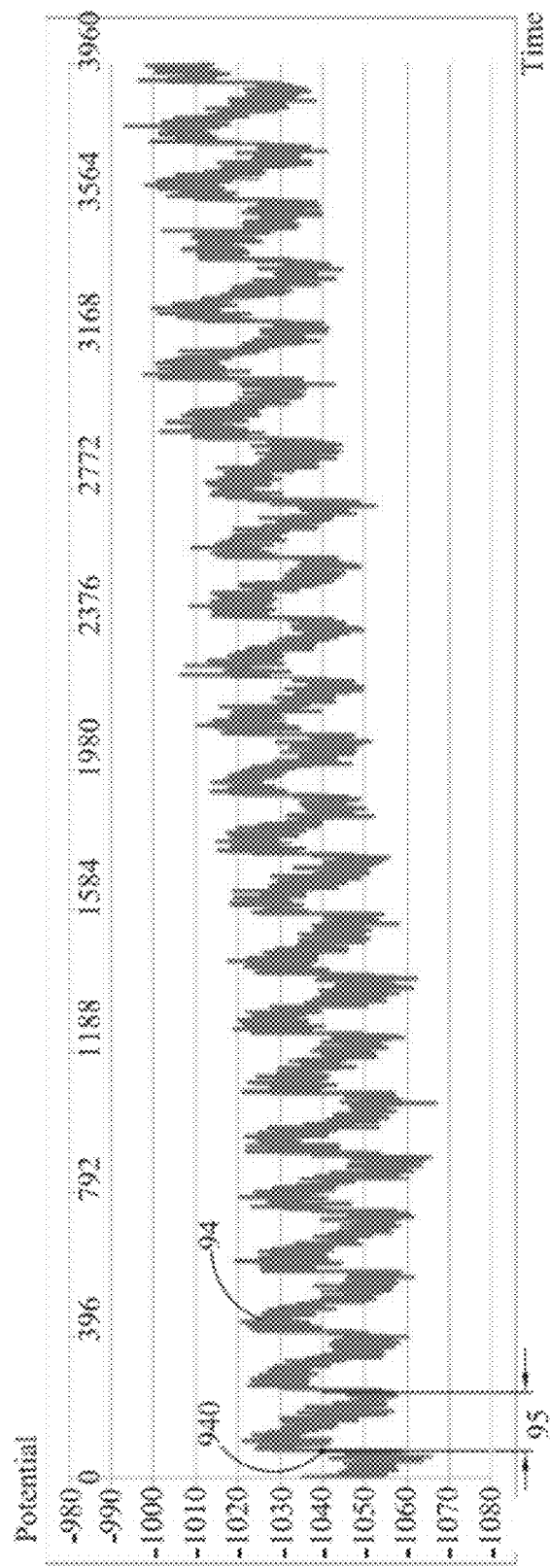

Please refer to FIGS. 7A and 7B, which illustrate a processed signal sequence with respect to a related position within the plurality of fluorescent images. In FIG. 7A, a plurality of processed images 93b after the spatial filtering process are shown, wherein the image area 931 on each processed image 93b is corresponding to a related position (250 of the organic object 25. It is noted that the other related positions (other grids except the grid labeled as numeral 250) have a corresponding image area according to the rule shown in FIG. 7A, respectively. The control module performs calculation process on each image area within each processed image for converting the brightness value of the pixels within each image area 931 into potential signal and recombining the potential signal into a recombined signal, thereby forming a plurality of signal sequences associated with the plurality of the specific areas of the organic object 25, respectively. The calculation process for converting the brightness value into cellular membrane potential is a well-established process which will not be further described hereinafter. In FIG. 7B, it illustrates one of the signal sequence 94 with respect to the related position 250 on the organic object 25, wherein the signal sequence 94 is composed of a plurality of recombined potential signals 95, and each of recombined potential signal 95 is composed by a plurality of potential signals 940 which are respectively corresponding to the brightness value of the image areas 931 of the plurality of processed images 93b. It is noted that the potential signals 940 may be explained as the $s_0$~$s_7$ shown in FIG. 4B.

Figure 8:
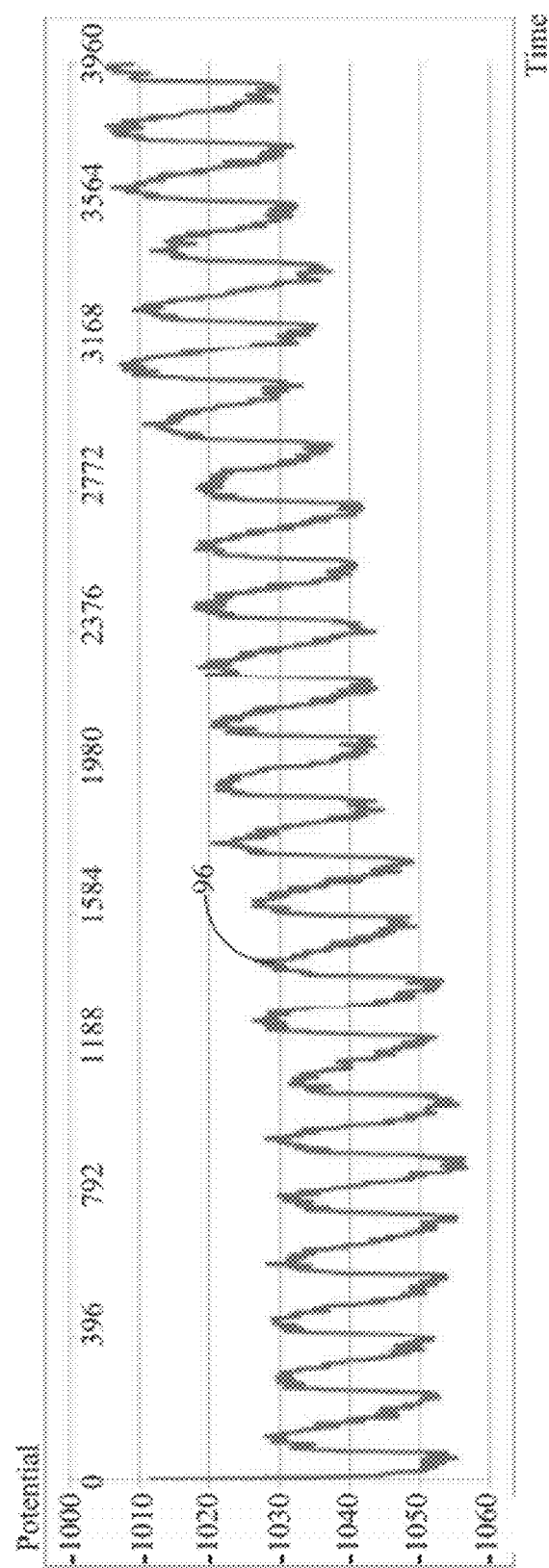
FIG. 8 shows the processed signal sequence according to the present invention.

However, as illustrated in FIG. 7B, the control module can further performs a time filtering process on each signal sequence so as to reduce the noise interferences, thereby obtaining a processed signal sequence 96 shown in FIG. 8. It is noted that the filter for performing the time filtering process can be, but should not be limited to, a Butterworth low-pass filter for processing each signal sequence. During the inspection on the organic object by using the system shown in FIG. 2A, 2B, or 2C, once an abnormality is occurred in the organic object, the sequential action potential generated from the pacing organic object by the second pulse signals will be varied to cause variation of membrane potential such that the chemical resonance structure of the dye within the organic object is changed thereby causing the variation of the fluorescent light generated by the dye. Once the variation of the fluorescent light is acquired by the image acquiring unit, the control module can determine electrophysiology of the organic object according to the signal sequences or the processed signal sequences. Since each signal sequence or processed signal sequence is corresponding to the related position of the organic object in visible surface of optical unit, while the recorded signal sequences can assist researchers in studying the electrophysiologic abnormality.

The foregoing embodiments are practiced by implementing impressing means such as depressant or depressing elements on the organic object for preventing vibration of the organic object. It is noted that the stroboscopic optical image mapping system in the present invention can also be utilized on the organic object without depressing means. For example, "Characteristics of motion artifacts in cardiac optical mapping studies, 31 Annual International Conference of IEEE EMBS Minneapolis, Minn., USA, Sep. 2-6, 2009" disclosed by the Martin et al., or "High resolution optical mapping of cardiac action potentials in freely beating rabbit hearts, Proceeding of the $26^{th}$ Annual International Conference of the IEEE EMBS San Francisco, Calif., USA, Sep. 1-5, 2004" disclosed by Inagaki et al. are all about the ways for acquiring the clear fluorescent images without using depressing means for depressing the vibration of the organic object. Once the images are obtained by the method provided by the Martin et al. or Inagaki et al., the image and signal processing of the present invention can also be implemented for determining if the organic object is under its normal condition or not.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

What is claimed is:

1. A stroboscopic optical image mapping system, comprising:
    a control module performing a delay control on a first pulse signal which has a plurality of pulses formed by a pulse period, thereby generating a delayed pulse signal, wherein a time interval between two adjacent pulses of the delayed pulse signal has a first time difference with respect to the pulse period;

a light source module providing an incident light to be projected on an organic object with a dye contained therein, wherein the organic object is stimulated by a second pulse signal thereby generating a sequential action potential, and the incident light excites the dye inside the organic object such that the organic object generates a fluorescent light corresponding to the intensity of the sequential action potential; and an image acquiring unit coupled to the control module, the image acquiring unit acquiring the fluorescent light according to the delayed pulse signal thereby forming a plurality of fluorescent images.

2. The system according to claim 1, further comprising a depressing means for preventing the organic object from vibration, wherein the depressing means is selected from a group consisting of a depressant and a depressing element.

3. The system according to claim 1, wherein the second pulse signal is a physiological signal generated by the organic object or is an external pulse signal provided by an electrical stimulator.

4. The system according to claim 1, wherein the control module further comprises:

a controller providing the first pulse signal; and a delay unit coupled to the controller and the image acquiring unit, the delay unit performing the delay control so as to adjust a triggering time of the first pulse signal.

5. The system according to claim 4, wherein the delay unit is further coupled to the light source module, and the light source module receives the delayed pulse signal, thereby generating the incident light corresponding to the delayed pulse signal.

6. The system according to claim 1, wherein control module further receives the plurality of fluorescent images, and the control module performs a spatial filtering process on the plurality of fluorescent images so as to form a plurality of processed images.

7. The system according to claim 6, wherein the spatial filtering process is selected from a group consisting of Gaussian smooth process, pixel average process and a combination of Gaussian smooth process and pixel average process.

8. The system according to claim 6, wherein the control module performs a calculation process on the plurality processed images for generating a plurality of signal sequences, which are corresponding to a related position of the organic object in visible surface of organic object, respectively, wherein each signal sequence comprises a plurality of recombined potential signals, each of which is formed by a plurality of segment signals, respectively, corresponding to one of the processed images.

9. The system according to claim 8, wherein the control module performs a time filtering process on each signal sequence, thereby forming a processed signal sequence.

10. The system according to claim 9, wherein the time filtering process is performed by using a Butterworth lowpass filter for filtering each signal sequence.

11. The system according to claim 8, wherein the sequential action potential is composed of a plurality of action potential wavelets, and a second time difference between the adjacent recombined potential signals is equal to a time period of the at least one action potential wavelet.

12. The system according to claim 1, wherein the sequential action potential is composed of a plurality of action potential wavelets, wherein at least one pulse of the delayed pulse signal is generated within a wavelet period of each action potential wavelet.

13. A stroboscopic optical image mapping system, comprising:

a control module performing a delay control on a first pulse signal which has a plurality of pulses formed by a pulse period, thereby generating a delayed pulse signal, wherein a time interval between two adjacent pulses of the delayed pulse signal has a first time difference with respect to the pulse period;

a light source module coupled to the control module, the light source module providing an incident light to be projected on an organic object with a dye contained therein, wherein the organic object is stimulated by a second pulse signal thereby generating a sequential action potential, and the incident light excites the dye inside the organic object such that the organic object generates a fluorescent light corresponding to the intensity of the sequential action potential; and an image acquiring unit acquiring the fluorescent light so as to form a plurality of fluorescent images.

14. The system according to claim 13, further comprising a depressing means for preventing the organic object from vibration, wherein the depressing means is selected from a group consisting of a depressant and a depressing element.

15. The system according to claim 13, wherein the second pulse signal is a physiological signal generated by the organic object or it is an external pulse signal provided by an electrical stimulator.

16. The system according to claim 13, wherein the control module further comprises:

a controller providing the first pulse signal; and a delay unit coupled to the controller and the light source module, the delay unit performing the delay control so as to adjust a triggering time of the first pulse signal.

17. The system according to claim 13, wherein the control module further receives the plurality of fluorescent images, and the control module performs a spatial filtering process on the plurality of fluorescent images so as to form a plurality of processed images.

18. The system according to claim 17, wherein the spatial filtering process is selected from a group consisting of Gaussian smooth process, pixel average process and a combination of Gaussian smooth process and pixel average process.

19. The system according to claim 17, wherein the control module performs a calculation process on the plurality processed images for generating a plurality of signal sequences, which are corresponding to a related position of the organic object in visible surface of organic object, respectively, wherein each signal sequence comprises a plurality of recombined potential signals, each of which is formed by a plurality of segment signals, respectively, corresponding to one of the processed images.

20. The system according to claim 19, wherein the control module performs a time filtering process on each signal sequence thereby forming a processed signal sequence.

21. The system according to claim 20, wherein the time filtering process is performed by using a Butterworth lowpass filter for filtering each signal sequence.

22. The system according to claim 19, wherein the sequential action potential is composed of a plurality of action potential wavelets, and a second time difference between the adjacent recombined potential signals is equal to a time period of the at least one action potential wavelet.

23. The system according to claim 13, wherein the sequential action potential is composed of a plurality of action potential wavelets, wherein at least one pulse of the delayed pulse signal is generated within a wavelet period of each action potential wavelet.

* * * * *

UNITED STATES PATENT AND TRADEMARK OFFICE
CERTIFICATE OF CORRECTION

| | | |
|---|---|---|
| PATENT NO. | : 8,487,274 B2 | Page 1 of 1 |
| APPLICATION NO. | : 13/473820 | |
| DATED | : July 16, 2013 | |
| INVENTOR(S) | : Liang-Chia Chen et al. | |

It is certified that error appears in the above-identified patent and that said Letters Patent is hereby corrected as shown below:

On the title page, item 73 the assignees on the record should be the following two assignees:

NATIONAL TAIPEI UNIVERSITY OF TECHNOLOGY, TAIPEI, TAIWAN

MACKAY MEMORIAL HOSPITAL, TAIPEI CITY, TAIWAN

Signed and Sealed this
Twenty-second Day of October, 2013

Teresa Stanek Rea
*Deputy Director of the United States Patent and Trademark Office*